United States Patent [19]
Greer et al.

[11] Patent Number: 5,790,427
[45] Date of Patent: Aug. 4, 1998

[54] EVENT HISTORY DATA ACQUISITION

[75] Inventors: David A. Greer, Simpsonville; David E. Schweikert, Moore, both of S.C.

[73] Assignee: Westinghouse Air Brake Company, Wilmerding, Pa.

[21] Appl. No.: 520,464

[22] Filed: Aug. 28, 1995

[51] Int. Cl.$^6$ .............................. G11B 20/10; A61N 1/37
[52] U.S. Cl. .......................... 364/556; 364/550; 607/27
[58] Field of Search .............................. 364/556, 927.2, 364/928, 942.7, 920, 926.9, 927.5, 939, 964, DIG. 1, DIG. 2, 550, 551.01; 395/200.01, 200.08, 200, 200.43, 843; 607/27

[56] References Cited

U.S. PATENT DOCUMENTS

| | | | |
|---|---|---|---|
| 4,258,421 | 3/1981 | Juhasz et al. | 364/424 |
| 4,379,339 | 4/1983 | Narita | 364/900 |
| 4,596,255 | 6/1986 | Snell et al. | 607/27 |
| 4,672,613 | 6/1987 | Foxworthy et al. | 364/200 |
| 4,745,564 | 5/1988 | Tennes et al. | 364/550 |
| 4,773,401 | 9/1988 | Citak et al. | 607/27 |
| 4,794,548 | 12/1988 | Lynch et al. | 364/550 |
| 5,040,534 | 8/1991 | Mann et al. | 607/27 |
| 5,128,885 | 7/1992 | Janis et al. | 364/945.3 |
| 5,239,646 | 8/1993 | Kimura | 395/575 |
| 5,426,774 | 6/1995 | Banerjee et al. | 395/575 |
| 5,431,691 | 7/1995 | Snell et al. | 607/27 |
| 5,530,898 | 6/1996 | Miyake | 395/834 |

*Primary Examiner*—Emanuel T. Voeltz
*Assistant Examiner*—Bryan Bui
*Attorney, Agent, or Firm*—James Ray & Associates

[57] ABSTRACT

An event data recorder and method for recording data relating to a distinct event which pertains to operation of a mechanism. The recorder comprises a device for collecting data pertaining to such operation and formatting such data into a sequence of data elements. A circular buffer is linked to the collecting and formatting device for temporarily storing a number of data elements. The elements are stored on the buffer as a newest element continuously writes over an oldest element as a storage limit of the buffer is reached. The recorder also includes a timer of predetermined duration which activates upon each occurrence of such event. The recorder has a memory device for retaining the data elements. The elements can be accessed therefrom for analysis of such operation of such mechanism surrounding such event. The recorder further includes a data element transfer device, connected to the timer, for transferring the elements from the buffer to the memory device wherein for each occurence of such event a preselected number of the data elements stored prior to, and including, an instant the timer deactivates is transferred by the transfer device from the buffer to the memory device. A data log is thereby formed within the memory device from which the elements may be accessed for analysis of such operation of such mechanism.

22 Claims, 5 Drawing Sheets

EVENT HISTORY DATA ACQUISITION

FIELD OF THE INVENTION

The present invention generally relates to a data recording system used to store data pertaining to operation of a mechanism and, more particularly, is concerned with an event history data recorder and method for recording data relating to a distinct event and pertaining to operation of a mechanism preceding and following each occurrence of such distinct event.

BACKGROUND OF THE INVENTION

Data recorders, data loggers, and event recorders have been in widespread use in various industries for several years prior to the present invention. These devices have been, and continue to be, used to store input and/or output data pertaining to the operation of a myriad of mechanisms. Typical applications include aircraft, water craft, automobiles, buses, passenger transit vehicles, railcar train consists and a multitude of other machines. Data recording technology has also been applied to other fields including electrocardiograph (EKG) and electroencephalograph (EEG) machines, blood pressure meters, and other biomedical instruments. No matter the application, data recorders are ultimately utilized to store data so that such data may be accessed and analyzed, if necessary, at a later time.

Typical data recording systems record all or a certain set of input/output data continuously for extended periods of time. Large amounts of memory space are therefore generally required to accommodate the volume of data to be recorded. Such data recording systems continuously record data in a circular buffer with the newest data writing over and destroying the oldest data when the storage limit of the circular buffer is reached. Consequently, data that may be especially pertinent to a distinct event or condition may be destroyed before the opportunity is had to study such data and ascertain the underlying causes of the event or condition.

The data recorded by such typical data recording systems is usually not related to any distinct event. Such data recording systems, moreover, do not provide a direct means for indicating when any such distinct event may have occurred. Consequently, when such recorded data is to be accessed and analyzed, an investigator must wade through hours or even days worth of data before locating the portion of data relevant to a particular inquiry.

The present invention is related to typical data recording systems in that it too records input/output data for later analysis. Whereas such input/output data recorded by such typical data recording systems relates only generally to the operation of such mechanism being monitored, the present invention, however, records data relating specifically to a distinct event. Whereas typical data recording systems record all or a certain set of input/output data continuously for hours or even days, the present invention records data only from the start of a prespecified time period before to the end of a predetermined time period after a distinct event occurs. Whereas such typical data recording systems eventually destroy data when storage limits of its circular buffer are reached, the present invention transfers data relating to such distinct event from a circular buffer to a memory device. The data recorded within the memory device is not destroyed unless it is overwritten by data relating to another occurrence of the same distinct event.

A first embodiment of the present invention, as alluded to in the preceding paragraphs and as fully set forth hereinafter, records data relating to a single distinct event. A presently preferred second embodiment, set forth below, records data relating to a plurality of distinct events. In either embodiment, any one distinct event may be devoted to a specific condition or a part of a diagnostic system. For example, numerous parameters associated with the operation of any given mechanism, such as those listed in the preceding paragraphs, can be monitored. Fluctuation of one or more parameters above or below specifications could be chosen to constitute a distinct event. Likewise, fluctuation of one or more other parameters above or below specifications may be selected to comprise another distinct event. Therefore, the distinct events may be individually formulated according to the requirements of the particular mechanism to be monitored.

It should be noted that determining which parameters to use in formulating any given distinct event is not necessary to an understanding of the instant invention. Persons skilled in the data recording art should easily be able to formulate the distinct events to suit the requirements of any given mechanism.

SUMMARY OF THE INVENTION

In a first embodiment, the present invention provides an event history data recorder for recording data relating to a distinct event and pertaining to operation of a mechanism preceding and following each occurrence of such distinct event. The recorder includes a means for collecting data pertaining to such operation of such mechanism and relating to such distinct event and for formatting such collected data into a sequence of data elements. The recorder also includes a circular buffer linked to the collecting and formatting means for temporarily storing a predetermined number of the data elements. The data elements are continuously stored on the circular buffer as a newest data element continuously writes over an oldest data element as a storage limit of the circular buffer is reached and as the circular buffer so continuously stores. The recorder additionally includes a timer of predetermined duration activated upon each occurrence of such distinct event for the predetermined duration. The recorder next includes a memory device for retaining the data elements and from which the data elements can be accessed for analysis of such operation of such mechanism surrounding such distinct event. The recorder further includes a means, connected to the timer, for transferring the data elements from the circular buffer to the memory device. For each occurrence of such distinct event, a preselected number of the data elements stored prior to, and including, an instant the timer deactivates is transferred by the transferring means from the circular buffer to the memory device thereby forming a data log within the memory device from which the data elements recorded therein may be accessed for analysis of such operation of such mechanism.

In a presently preferred second embodiment, the present invention provides an event history data recorder for recording data relating to a plurality of distinct events and pertaining to operation of a mechanism preceding and following each occurrence of each such distinct event. The recorder includes a means for collecting data pertaining to such operation of such mechanism and relating to each such distinct event and for formatting such collected data into a sequence of data elements for each such distinct event for which data is to be recorded. One data element from one such distinct event is formed nearly coincidently as another data element from each of all other such distinct events such that the nearly coincidently formed data elements constitute a set of temporally related data elements. The recorder also includes a circular buffer, linked to the collecting and formatting means, having a plurality of tracks each of which designated for storing temporarily a preset number of the data elements relating to one of such distinct events so that the data elements relating to such distinct events are aligned to form the sets of temporally related data elements. The sets of temporally related data elements are continuously stored on the circular buffer as a newest set of temporally related data elements continuously writes over an oldest set of temporally related data elements as a storage limit of the circular buffer is reached and as the circular buffer so continuously stores. The recorder additionally includes a timer of predetermined duration for each such distinct event so that as each such distinct event occurs the timer individually corresponding thereto activates for the predetermined duration. The recorder next includes a memory device having a plurality of memory locations each of which dedicated to retaining the data elements temporarily stored on one of the tracks of the circular buffer when such distinct event to which the data elements relate occurs. The recorder further includes a means, connected to each of the timers, for transferring the data elements from the tracks of the circular buffer to the dedicated memory locations. As the timers individually corresponding to such distinct events deactivate, the transferring means transfers from the tracks to the dedicated memory locations a preselected number of the data elements for each of such distinct events so occurred. A data log is thereby essentially formed within each of the dedicated memory locations. From each of the data logs the data elements relating to one of such distinct events may be accessed for analysis of such operation of such mechanism.

The present invention also provides a method for the selective recordation of data relating to a distinct event and pertaining to operation of a mechanism preceding and following each occurrence of such distinct event. This method, for carrying out the first embodiment of the present invention, includes the steps of collecting data pertaining to such operation of such mechanism and relating to such distinct event; formatting such collected data into a sequence of data elements; and assigning sequentially and incrementally to each of the data elements an index number thereby forming a sequence of index number-data element units. The method also includes the step of storing temporarily on a circular buffer a preset number of the index number-data element units as a newest index number-data element unit continuously writes over an oldest index number-data element unit as a storage limit of the circular buffer is reached and as the circular buffer so continuously stores. The method additionally includes setting a retain event log flag to true when the data elements relating to such distinct event are to be recorded in a memory device; setting an event active flag to true when such distinct event occurs; and activating a timer of predetermined duration when both the retain event log and the event active flags are set to true. The method next includes the steps of denoting a stop index number as the index number contained within the index number-data element unit being stored onto the circular buffer at an instant the timer deactivates upon expiration of the predetermined duration and denoting a start index number as the stop index number plus one less a preselected number. The method further includes transferring, for each occurrence of such distinct event, from the circular buffer to the memory device the data elements, in the sequence of index number-data element units, located between and including the start and the stop index numbers. A data log is thereby essentially formed within the memory device. From the data log, the data elements relating to such distinct event may be accessed for analysis of such operation of such mechanisms.

The present invention further provides a method for the selective recordation of data relating to the plurality of distinct events and pertaining to operation of such mechanism preceding and following each occurrence of each such distinct event. This method, for carrying out the presently preferred second embodiment of the present invention, includes the steps of collecting data pertaining to such operation of such mechanism and relating to each such distinct event and formatting such collected data into a sequence of data elements for each such distinct event for which data is to be recorded. The sequences are formatted so that one of the data elements from one such distinct event is formed nearly coincidently as another one of the data elements from each of all other such distinct events such that the nearly coincidently formed data elements constitute a set of temporally related data elements. The method also includes the step of assigning sequentially and incrementally an index number to each of the sets of temporally related data elements so as to form a sequence of index number-set units. The method additionally includes the step of storing temporarily on one of a plurality of tracks of a circular buffer the assigned index numbers and on each of all other tracks a preset number of the data elements relating to one of such distinct events so that the assigned index numbers and the data elements relating to such distinct events are aligned to form the sequence of index number-set units. The index number-set units are continuously stored on the circular buffer as a newest index number-set unit continuously writes over an oldest index number-set unit as a storage limit of the circular buffer is reached and as the circular buffer so continuously stores. The method next includes the step of setting, for each such distinct event, a retain event log flag to true when the data elements relating to such distinct event are to be retained in a memory location dedicated to such distinct event The memory location is one of a plurality of memory locations within a memory device. Each of the memory locations is dedicated to one of such distinct events. The method further includes the steps of setting, for each such distinct event, an event active flag to true when such distinct event occurs and activating, for each such distinct event, a timer of predetermined duration when both the retain event log and the event active flags for such distinct event are set to true. The method also includes the steps of denoting, for each such distinct event so occurred, a stop index number as the index number contained within the index number-set unit being stored onto the circular buffer at an instant the timer corresponding to such distinct event deactivates; denoting, for each such distinct event so occurred, a start index number as the stop index number plus one less a preselected number; and, for each such distinct event so occurred, transferring the data elements located between and including the start and stop index numbers from the track to the corresponding dedicated memory location for each occurrence of such distinct event. Data logs are essentially formed with each of the memory locations for each of the distinct events that occurred. Each of the data logs, like the memory locations, is dedicated to retaining the data elements relating to one of such distinct events. The data elements relating to such distinct events may therefore be accessed from the data logs for analysis of such operation of such mechanism.

OBJECTS OF THE INVENTION

A primary object of the present invention is to provide an event history data recorder for recording data relating to a plurality of distinct events and pertaining to operation of a mechanism preceding and following each occurrence of each such distinct event.

Another object of the present invention is to provide a method for the selective recordation of data relating to a plurality of distinct events and pertaining to operation of a mechanism preceding and following each occurrence of each such distinct event.

Yet another object of the present invention is to provide an event history data recorder that records data relating to a plurality of distinct events wherein for each such distinct event a data log for containing the data so recorded is updated each occurrence of such distinct event.

Even another object of the present invention is to provide an event history data recorder for recording data relating to a plurality of distinct events wherein for each such distinct event a data log for containing the data so recorded is formed for each occurrence of such distinct event until a storage capacity is reached at which time said data logs for each such distinct event are updated in a general order in which said data logs were formed.

Still another object of the present intention is to provide an event history data recorder for recording data relating to a distinct event and pertaining to operation of a mechanism preceding and following each occurrence of such distinct event.

A further object of the present invention is to provide a method for the selective recordation of data relating to a distinct event and pertaining to operation of a mechanism preceding and following each occurrence of such distinct event.

Yet a further object of the present invention is to provide an event history data recorder that records data relating to a distinct event wherein a data log for containing the data so recorded is updated each occurrence of such distinct event.

Even a further object of the present invention is to provide an event history data recorder for recording data relating to a distinct event wherein a data log for containing the data so recorded is formed for each occurrence of such distinct event until a storage capacity is reached at which time said data logs are updated in an order in which said data logs were formed.

Still a further object of the present invention is to provide an event history data recorder that records data relating to a plurality of distinct events and such distinct events for which data is to be recorded may be selected.

An additional object of the present invention is to provide an event history data recorder that records data relating to a plurality of distinct events and for each of such distinct events the recorder records only from the start of a prespecified time period before to the end of a predetermined time period after such distinct event occurs.

Yet an additional object of the present invention is to provide an event history data recorder that requires less storage capacity than typical data recorders, data loggers and/or event recorders.

In addition to the various objects and advantages of the present invention described above, it should be noted that various other objects and advantages of the present invention will become more readily apparent to those persons who are skilled in the data recorder art from the detailed description of the invention, particularly when such description is taken in conjunction with the attached drawings and with the appended claims.

DETAILED DESCRIPTION OF THE INVENTION

Prior to proceeding to the more detailed description of the various embodiments of the present invention, for the sake of clarity and understanding of the invention, it should be noted that identical components having identical functions in each of the accompanying drawings have been identified with identical reference numerals throughout each of the Figures illustrated herein.

Figure 1:
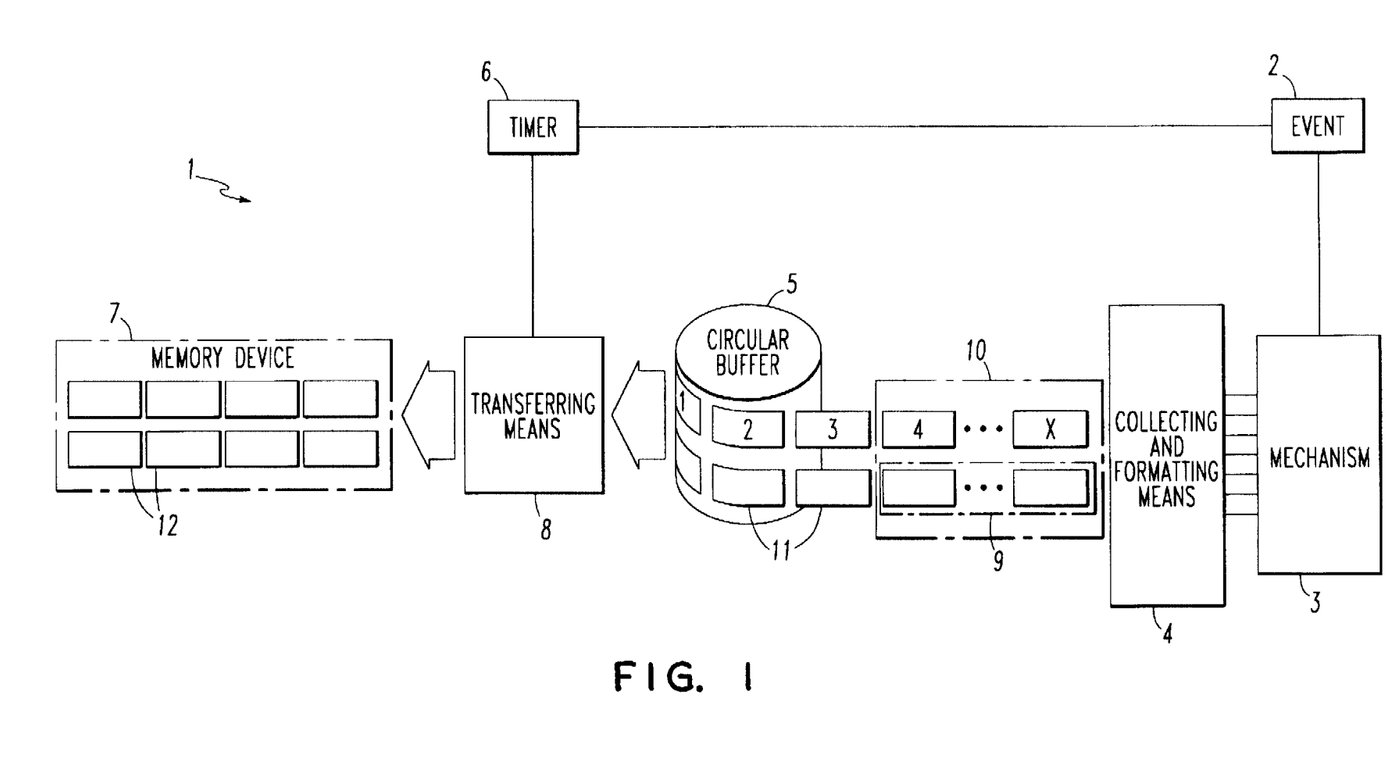
FIG. 1 is a schematic block diagram of a first embodiment of the present invention.
Figure 2:
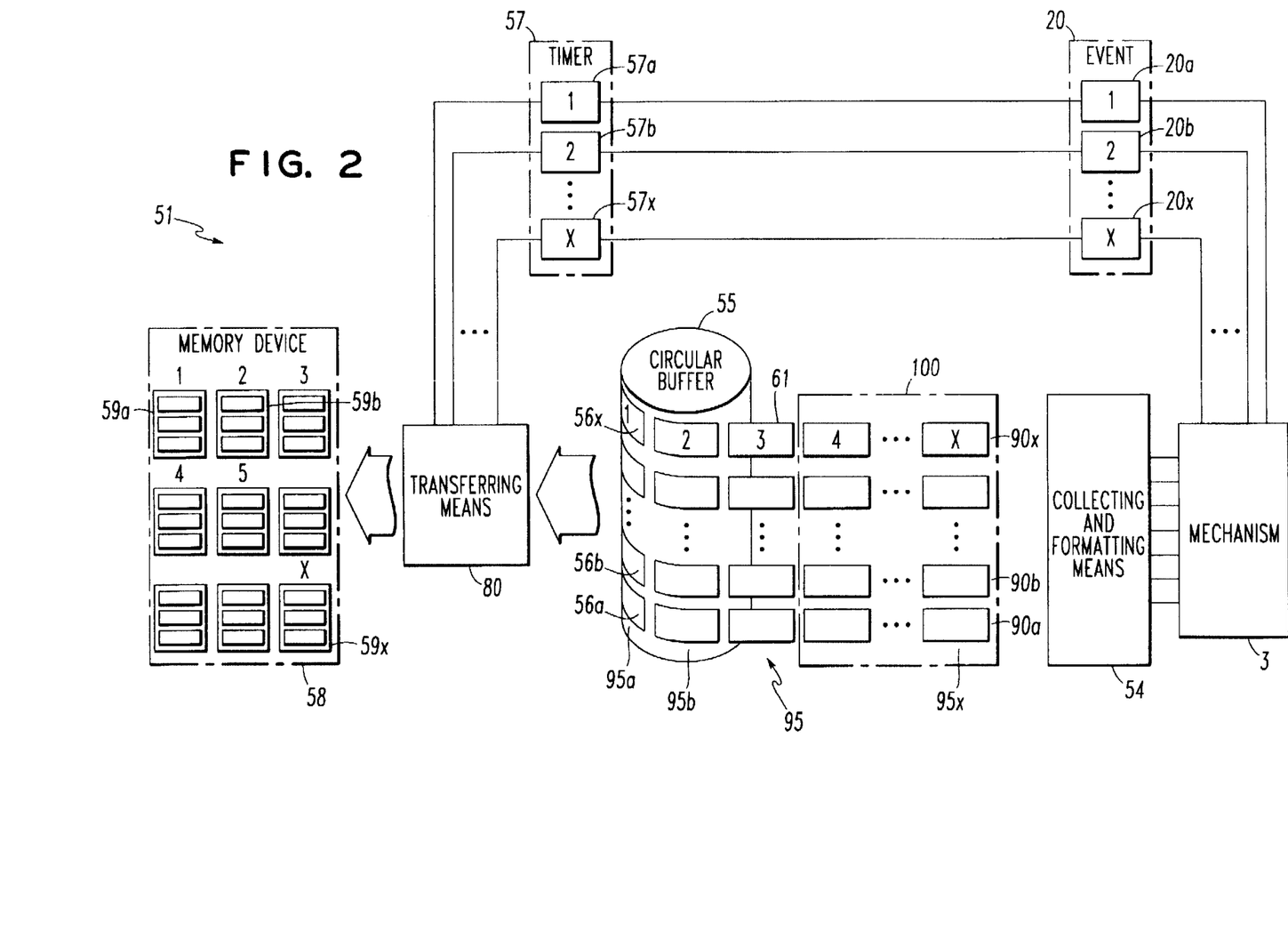
FIG. 2 is a schematic block diagram of a presently preferred second embodiment of the present invention.

Referring to FIGS. 1 and 2, illustrated therein are the essential details of a first embodiment and a presently preferred second embodiment, respectively, of the present invention. FIG. 1 illustrates an event history data recorder, generally designated 1, for recording data relating to a distinct event 2 and pertaining to operation of a mechanism 3 preceding and following each occurrence of such distinct event 2. FIG. 2 illustrates an event history data recorder, generally designated 51, for recording data relating to a plurality of distinct events, generally designated 20, and pertaining to such operation of such mechanism 3 preceding and following each occurrence of each such distinct event 20.

Figure 3:
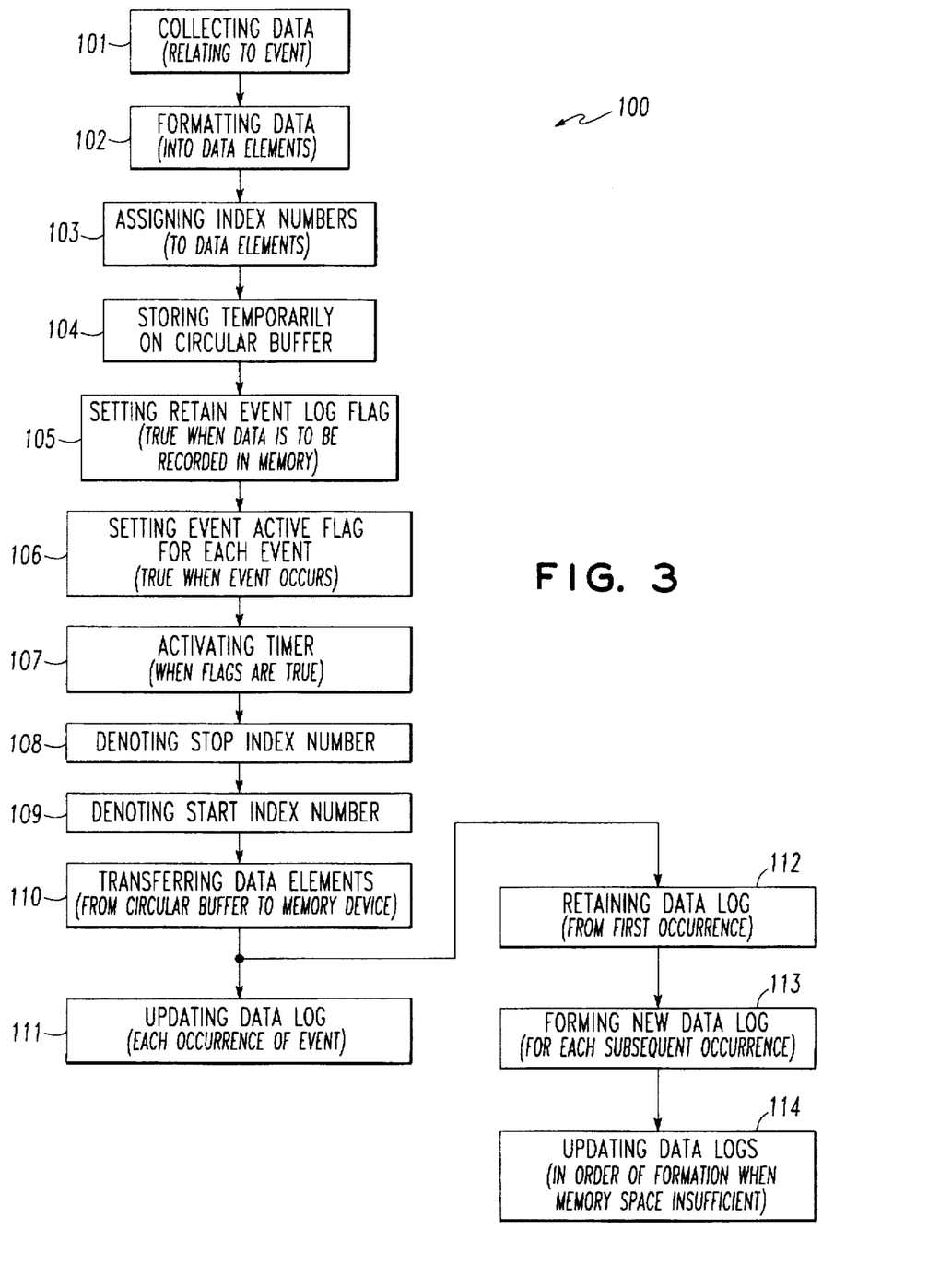
FIG. 3 is a flow chart outline of a method for carrying out the first embodiment of the present invention.
Figure 4:
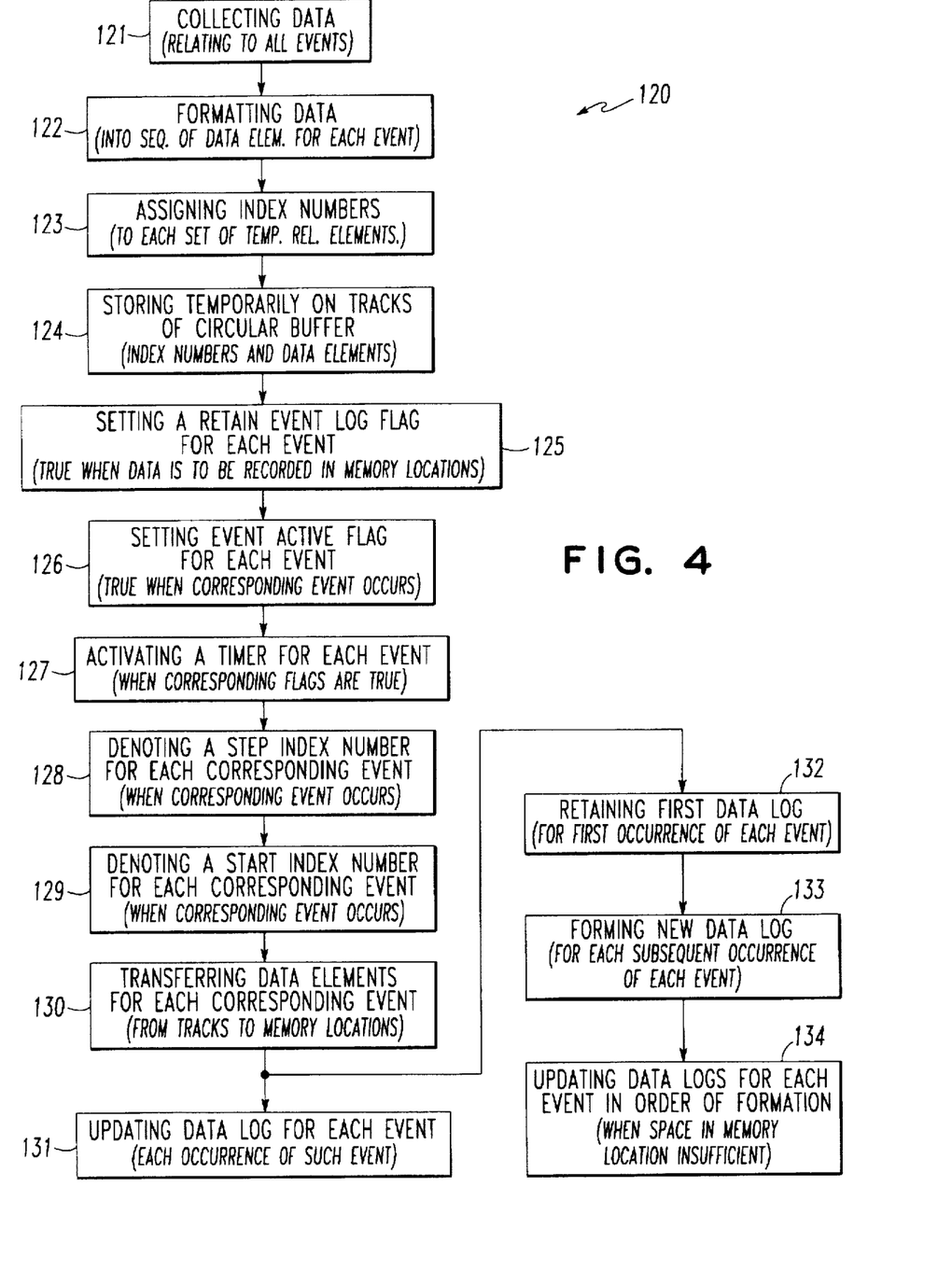
FIG. 4 is a flow chart outline of a method for carrying out the presently preferred second embodiment of the present invention.
Figure 5:
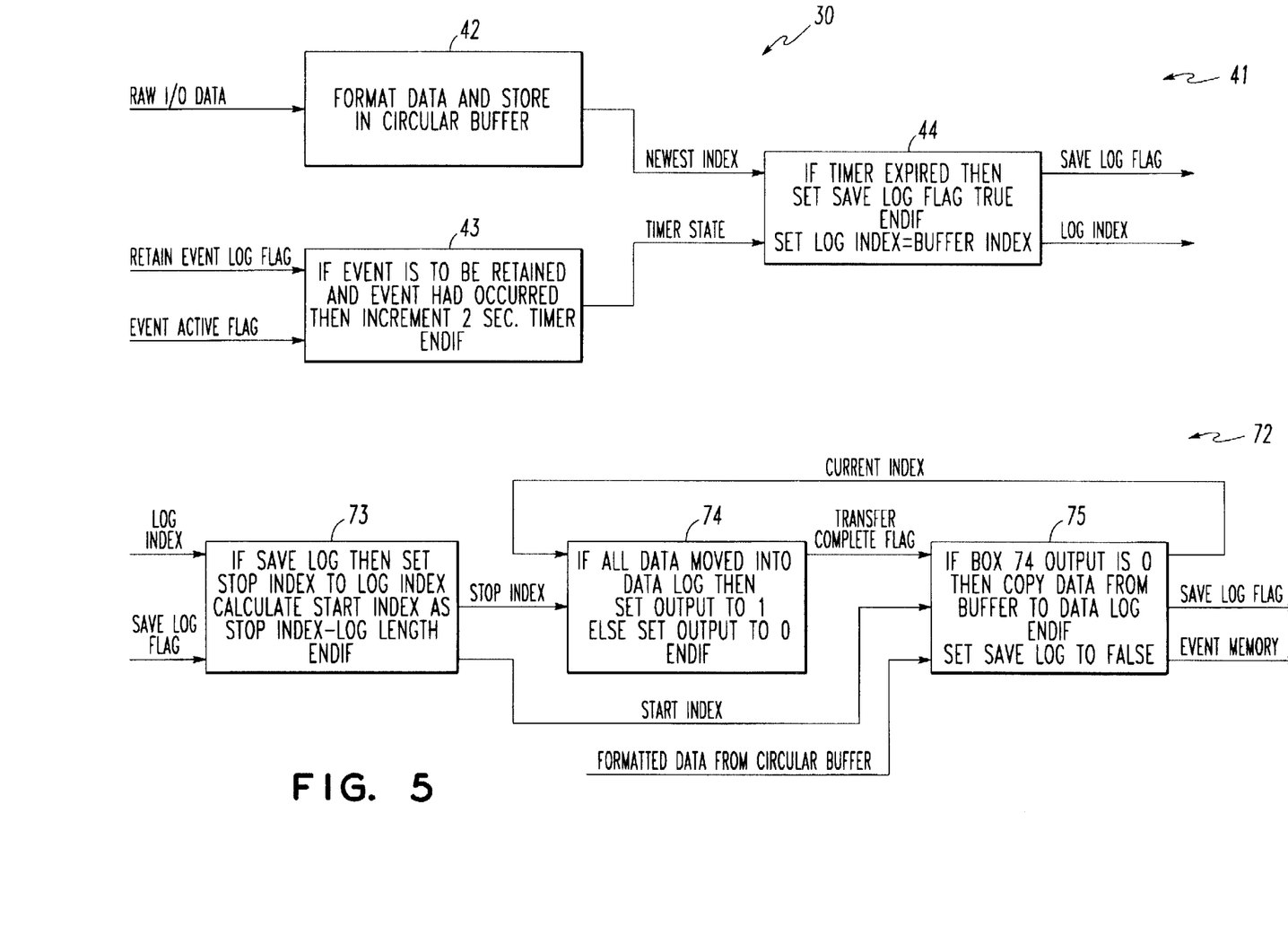
FIG. 5 illustrates in a block diagram form the logic underlying the implementation of the methods for carrying out the present invention.

Referring to FIGS. 3 and 4, illustrated therein in flow chart form are the essential details of a method for carrying out the first embodiment and a method for carrying out the presently preferred second embodiment, respectively, of the present invention. FIG. 3 illustrates the method for the selective recordation of data relating to such distinct event and pertaining to operation of such mechanism preceding and following each occurrence of such distinct event. FIG. 4 illustrates the method for the selective recordation of data relating to the plurality of distinct events and pertaining to operation of such mechanism preceding and following each occurrence of each such distinct event. FIG. 5 illustrates in a block diagram form the logic underlying the implementation of the methods for carrying out the present invention.

Refer now to the first embodiment of the present invention illustrated in FIG. 1. In the first embodiment, the event history data recorder 1 includes a collecting and formatting means 4, a circular buffer 5, a timer 6 of a predetermined duration, a memory device 7 and a transferring means 8. The collecting and formatting means 4 collects data pertaining to such operation of such mechanism 3 and relating to such distinct event 2 and formats such collected data into a sequence of data elements 9. The collecting and formatting means 4 also assigns sequentially and incrementally an index number to each of the data elements as such collected data is formatted into the sequence of data elements 9 so as to form a sequence of index number-data element units 10. The circular buffer 5, linked to the collecting and formatting means 4, temporarily stores a preset number 11 of the index number-data element units. The preset number 11 of the index number-data element units are continuously stored on the circular buffer 5 as a newest index number-data element unit continuously writes over an oldest index number-data element unit as a storage limit of the circular buffer 5 is reached and as the circular buffer 5 so continuously stores. The timer 6 activates for the predetermined duration upon each occurrence of such distinct event 2. The transferring means 8 connects to the timer 6. As the timer 6 deactivates after each occurrence of such distinct event 2, the transferring means 8 transfers a preselected number of the data elements stored on the circular buffer 5 to the memory device 7. The preselected number of the data elements so transferred to, and retained 12 in, the memory device 7 are the data elements that were stored on the circular buffer 5 prior to, and including, an instant the timer 6 deactivated. The preselected number of data elements so retained 12 in the memory device 7 essentially form a data log within the memory device 7. The preselected number of data elements so retained 12 may be accessed from the data log for analysis of such operation of such mechanism 3 surrounding such distinct event 2.

A first technique for transferring the preselected number of the data elements stored on the circular buffer 5 to the memory device 7 involves using the index numbers. Specifically, the transferring means 8 denotes a stop index number as the index number contained within the index number-data element unit being stored onto the circular buffer 5 at such instant the timer 6 deactivates. Likewise, the transferring means 8 denotes a start index number as the stop index number plus one less the preselected number. The transferring means 8 then transfers each of the data elements stored on the circular buffer 5 located between and including the start index number and the stop index number to the memory device 7. The preselected number of data elements so transferred from the circular buffer 5 to the memory device 7 is referred to as a log length.

The present invention in essence waits for such distinct event 2 to occur and then records data relating to such distinct event 2. The data so recorded pertains to such operation of such mechanism 3 from the start of a prespecified time period before to the end of a predetermined time period after such distinct event 2 occurs. The predetermined time period is defined by and equal to the predetermined duration of the timer 6. The prespecified time period ends and the predetermined time period begins when the timer 6 activates. The predetermined time period ends when the timer 6 deactivates. The preselected number of data elements, and thus the log length, directly depends on the duration of the prespecified and predetermined time periods. For example, the present invention may be implemented having a prespecified time period of 5 seconds duration and a predetermined time period of 2 seconds duration. In such an implementation, the present data recorder would record 5 seconds of data before and 2 seconds of data after each occurrence of such distinct event 2. Assuming that the data elements are saved every 0.02 seconds, the log length would be 350 data elements. The log length is thus determined by the equation LL=(PS+PF)/RS where LL is the log length, PS is the duration of the prespecified time period in seconds, PF is the duration of the predetermined time period in seconds, and RS, expressed in seconds/data element, is the rate at which the data elements are saved.

In one variation of the first embodiment, the data log is updated each occurrence of such distinct event 2. The data log will therefore contain the data elements relating to the most recent occurrence of such distinct event 2.

In an alternative variation of the first embodiment, the data log formed when such distinct event 2 initially occurred is retained and a new data log is formed within the memory device 7 for each subsequent occurrence of such distinct event 2. The number of occurrences of such distinct event 2 for which data logs may be retained is directly dependent upon a storage capacity of the memory device 7. When there is no longer sufficient storage capacity within the memory device 7, the data logs are updated in the order in which they were formed.

In either variation, the memory device 7 may be realized in any one or more of several ways. For example, the memory device 7 may take the form of a battery backed random access memory (RAM) chip. Alternatively, the memory device 7 may be implemented using an electrically erasable programmable read only memory (EEPROM) chip. Those persons skilled in the data retention art should easily be able to select the manner in which to implement the memory device 7 so as to assure that the data elements are reliably retained.

Still referring to FIG. 1, the collecting and formatting means 4 may be implemented, among other ways, using a computer (not shown) connected to a plurality of sensors (not shown) and an analog to digital converter (not shown). The plurality of sensors monitor the parameters associated with, and generate analog signals corresponding to, such operation of such mechanism 3 relating to such distinct event 2. In this particular implementation, the analog to digital converter converts the analog signals into corresponding digital binary code and the computer formats the digital code into the data elements. Well known to practitioners skilled in the parameter monitoring and signal conversion art, further details of the monitoring and conversion functions are not necessary to recount herein. As with the collecting and formatting means 4, the transferring means 8 may also be implemented, among other ways, using a computer (not shown).

Referring now to FIG. 3, illustrated therein in flow chart form is the method, generally designated 100, for the selective recordation of data relating to such distinct event and pertaining to operation of such mechanism preceding and following each occurrence of such distinct event. The method 100 includes the steps of collecting 101 data pertaining to such operation of such mechanism and relating to such distinct event; formatting 102 such collected data into a sequence of data elements; and assigning 103 sequentially and incrementally to each of the data elements an index number thereby forming a sequence of index number-data element units. The method 100 also includes the step of storing temporarily 104 on a circular buffer a preset number of the index number-data element units as a newest index number-data element unit continuously writes over an oldest index number-data element unit as a storage limit of the circular buffer is reached and as the circular buffer so continuously stores. The method, 100 additionally includes setting 105 a retain event log flag to true when the data elements relating to such distinct event are to be recorded in a memory device; setting 106 an event active flag to true when such distinct event occurs; and activating 107 a timer of predetermined duration when both the retain event log and the event active flags are set to true. The method 100 next includes the steps of denoting 108 a stop index number as the index number contained within the index number-data element unit being stored onto the circular buffer at an instant the timer deactivates upon expiration of the predetermined duration and denoting 109 a start index number as the stop index number plus one less a preselected numbers The method 100 further includes transferring 110, for each occurrence of such distinct event, from the circular buffer to the memory device the data elements, in the sequence of index number-data element units, located between and including the start and the stop index numbers. Therefore, a data log is essentially formed from which the data elements relating to such distinct event may be accessed for analysis of such operation of such mechanism.

In one variation of the method 100, after the transferring step 110, the method 100 includes the step of updating 111 the data log each occurrence of such distinct event. The data log will therefore contain the data elements relating to the most recent occurrence of such distinct event.

In an alternative variation of the method 100, after the transferring step 110, the method 100 includes the steps of retaining 112 the data log formed when such distinct event initially occurred; forming 113 a new data log within the memory device for each subsequent occurrence of such distinct event; and when there is no longer sufficient space within the memory device, updating 114 the data logs in the order in which they were formed.

Refer now to the presently preferred second embodiment of the present invention illustrated in FIG. 2. In the presently preferred second embodiment, the event history data recorder 51 includes a collecting and formatting means 54; a circular buffer 55 having a plurality of tracks 56; a timer of a predetermined duration, generally designated 57, for each of such distinct events 20; a memory device 58 having a plurality of memory locations 59; and a transferring means 80. The collecting and formatting means 54 collects data pertaining to such operation of such mechanism 3 and relating to each of such distinct events 20. The collecting and formatting means 54 also formats such collected data into a sequence of data elements 90 for each of such distinct events 20 for which data is to be recorded. One data element from one such distinct event (e.g., 20a) is formed nearly coincidently as another one data element from each of all other such distinct events (e.g., 20a through 20x) such that the nearly coincidently formed data elements constitute a set of temporally related data elements (e.g., 95x). Each of the tracks 56 of the circular buffer 55 is designated to store temporarily a preset number 61 of the data elements relating to one of such distinct events 20 so that the data elements relating to such distinct events 20 are aligned to form the sets of temporarily related data elements 95. The collecting and formatting means 54 further assigns sequentially and incrementally an index number to each of the sets of temporally related data elements 95 as such collected data is formatted into the sequences of data elements 90 so as to form a sequence of index number-data element units 100. The circular buffer 55 also temporarily stores the preset number 61 of the index numbers on another track (e.g., 56x) so that the index number-set units 100 are continuously stored on the circular buffer 55 as a newest index number-set unit continuously writes over an oldest index number-set unit as a storage limit of the circular buffer 55 is reached and as the circular buffer 55 so continuously stores. As such distinct events 20 occur, the timers 57 individually corresponding thereto activate for the predetermined duration. For example, when such distinct event 20a occurs, the timer 57a activates for the predetermined duration. Likewise, when such distinct event 20x occurs, the timer 57x activates for the predetermined duration.

As previously mentioned, each sequence of data elements 90 relates to one of such distinct events 20. Similarly, each of the tracks 56 is designated to temporarily store the preset number 61 of data elements relating to one of such distinct events 20. Likewise, each of the memory locations 59 is dedicated to retaining the data elements temporarily stored on one of the tracks 56. Consequently, each of the memory locations 59 is dedicated to retaining the data elements relating to one of such distinct events 20. The transferring means 80 connects to each of the timers 57. As the timers 57 individually corresponding to such distinct events 20 deactivate, the transferring means 80 transfers from the designated tracks 56 to the dedicated memory locations 59 a preselected number of the data elements for each of such distinct events 20 that have occurred. The preselected number of data elements so retained in the dedicated memory locations 59 essentially form a data log within each of the memory locations 59. From each of the data logs the data elements relating to one of such distinct events 20 may be accessed for analysis of such operation of such mechanism 3.

A principal technique for transferring the preselected number of the data elements from the tracks 56 of the circular buffer 55 to the dedicated memory locations 59 involves using the index numbers. The principal transferring technique is a logical extension of the first transferring technique previously set forth in connection with the first embodiment. Specifically, the transferring means 80 denotes a stop index number, for each such distinct event 20 so occurred, as the index number contained within the index number-set unit being stored onto the circular buffer 55 when one of the timers 57 individually corresponding to one of such distinct events 20 deactivates. Likewise, the transferring means 80 denotes a start index number, for each such distinct event 20 so occurred, as the stop index number plus one less the preselected number. The stop and start index numbers, of course, are generated in pairs where each pair corresponds to one of such distinct events 20. For each such distinct event 20 so occurred, the transferring means 80 then transfers the data elements located between and including the start and stop index numbers from the tracks 56 to the dedicated memory locations 59. The preselected number of data elements so transferred between the tracks 56 and the memory locations 59 is referred to as a log length.

As manifested in the presently preferred embodiment, the present invention basically waits for one or more of such distinct events 20 to occur and then records data relating to such distinct events 20 that have occurred. The data so recorded pertains to such operation of such mechanism 3 from the start of a prespecified time period before to the end of a predetermined time period after each of such distinct events 20 occurred. The predetermined time period is defined by and equal to the predetermined duration of each of the timers 57. The prespecified time period may be of equal duration for each of such distinct events 20. The predetermined time periods may likewise be of equal duration. The prespecified time period ends and the predetermined time period begins for each of such distinct events 20 when the timers 57 individually corresponding to such distinct events 20 activate. The predetermined time period ends for each of such distinct events 20 when the timers 57 individually corresponding thereto deactivate. The preselected number of data elements, and thus the log length, directly depends on the duration of the prespecified and predetermined time periods. Therefore, as previously explained in connection with the first embodiment, the log length is governed by the equation LL=(PS+PF)/RS where LL is the log length, PS is the duration of the prespecified time period in seconds, PF is the duration of the predetermined time period in seconds, and RS is the rate at which the data elements are saved.

It should also be noted that, for the first embodiment as well as the presently preferred second embodiment, the prespecified time period before and the predetermined time period after such distinct event(s) occurs are variable and therefore may be changed to suit the requirements of a given application.

It should be further noted that, for the first embodiment as well as the presently preferred second embodiment, any one of a number of techniques for transferring the data elements from the circular buffer to the memory device may suffice for the purposes of the present invention. Those persons skilled in the data transfer art can select from such known techniques one appropriate to the circumstances encountered.

In one variation of the presently preferred second embodiment, for each occurrence of each such distinct event 20, the data log dedicated thereto is updated. For example, each time such distinct event 20a occurs, the data log 59a is updated with the data elements relating to such distinct event 20a. Likewise, each time such distinct event 20a occurs, the data log 59b is updated with the data elements relating to such distinct event 20b. The data logs will therefore contain the data elements relating to the most recent occurrences of such distinct events 20.

In an alternative variation of the presently preferred second embodiment, for each occurrence of each such distinct event 20, the data logs formed when such distinct events 20 initially occurred are retained and a new data log is formed within the memory locations 59 for each subsequent occurrence of each of such distinct events 20. For example, when such distinct event 20a initially occurs, a first data log is formed in memory location 59a. When such distinct event 20a occurs again, a second data log is formed in memory location 59a. Multiple data logs for the other such distinct events 20a through 20x are formed in the same manner.

The number of occurrences of such distinct events 20 for which data logs may be retained is directly dependent upon a storage capacity of the memory device 58. When there is no longer sufficient storage capacity within the memory device 58, the data logs for each of such distinct events 20 are updated generally in the order in which they were formed.

As with the first embodiment, the memory device 58 may be realized, anon other ways, in the form of a battery backed random access memory (RAM) chip or an electrically erasable programmable read only memory (EEPROM) chip. No matter how the memory device 58 is implemented, the goal is to select a type that assures reliable retention of the data elements.

Still referring to FIG. 2, as with the first embodiment, the collecting and formatting means 54 may be implemented, among other ways, using a computer (not shown) connected to a plurality of sensors (not shown) and an analog to digital converter (not shown). The plurality of sensors monitor the parameters associated with, and generate analog signals corresponding to, such operation of such mechanism 3 relating to each of such distinct events 20. In this particular implementation, the analog to digital converter converts the analog signals into corresponding digital binary code and the computer formats the digital code into the data elements. Well known to practitioners skilled in the parameter monitoring and signal conversion art, further details of the monitoring and conversion functions are not necessary to recount herein. As with the collecting and formatting means 54, the transferring means 80 may also be implemented, among other ways, using a computer (not shown).

One possible enhancement of the presently preferred second embodiment allows one to select (or deselect) any one or more of such distinct events 20 for which data is to be recorded. Specifically, one may choose all or only a certain number of such distinct events 20 for which data is to be recorded. Conversely, one may choose not to record data for a specific number of such distinct events 20.

Referring now to FIG. 4, illustrated therein in flow chart form is the method, generally designated 120, for the selective recordation of data relating to the plurality of distinct events and pertaining to operation of such mechanism preceding and following each occurrence of each such distinct event. The method 120 includes the steps of collecting 121 data pertaining to such operation of such mechanism and relating to each such distinct event and formatting 122 such collected data into a sequence of data elements for each such distinct event for which data is to be recorded. The sequences are formatted so that one of the data elements from one such distinct event is formed nearly coincidently as another one of the data elements from each of all other such distinct events such that the nearly coincidently formed data elements constitute a set of temporally related data elements. The method 120 also includes the step of assigning 123 sequentially and incrementally an index number to each of the sets of temporally related data elements so as to form a sequence of index number-set units. The method 120 additionally includes the step of storing 124 temporarily on one of a plurality of tracks of a circular buffer the assigned index numbers and on each of all other tracks a preset number of the data elements relating to one of such distinct events so that the assigned index numbers and the data elements relating to such distinct events are aligned to form the sequence of index number-set units. The index number-set units are continuously stored on the circular buffer as a newest index number-set unit continuously writes over an oldest index number-set unit as a storage limit of the circular buffer is reached and as the circular buffer so continuously stores. The method 120 next includes the step of setting 125, for each such distinct event, a retain event log flag to true when the data elements relating to such distinct event are to be retained in a memory location dedicated to such distinct event The memory location is one of a plurality of memory locations within a memory device. Each of the memory locations is dedicated to one of such distinct events. The method 120 further includes the steps of setting 126, for each such distinct event, an event active flag to true when such distinct event occurs and activating 127, for each such distinct event, a timer of predetermined duration when both the retain event log and the event active flags for such distinct event are set to true. The method 120 also includes the steps of denoting 128, for each such distinct event so occurred, a stop index number as the index number contained within the index number-set unit being stored onto the circular buffer at an instant the timer corresponding to such distinct event deactivates; denoting 129, for each such distinct event so occurred, a start index number as the stop index number plus one less a preselected number; and, for each such distinct event so occurred, transferring 130 the data elements located between and including the start and stop index numbers from the track to the corresponding dedicated memory location for each occurrence of such distinct event. Data logs are essentially formed with each of the memory locations for each of the distinct events that occurred. Each of the data logs, like the memory locations, is dedicated to retaining the data elements relating to one of such distinct events. The data elements relating to such distinct events may therefore be accessed from the data logs for analysis of such operation of such mechanism.

In one variation of the method 120, after the transferring step 130, the method 120 includes the step of updating 131, for each such distinct event, the data log each occurrence of such distinct event. Each data log will therefore contain the data elements relating to the most recent occurrence of one of such distinct events.

In an alternative variation of the method 120, after the transferring step, the method 120 includes the steps of retaining 132, for each such distinct event, the data log formed when such distinct event initially occurred; forming 133, for each such distinct event, a new data log within the memory device for each subsequent occurrence of such distinct event; and when there is no longer sufficient space within the memory device, updating 134, for each such distinct event, the data logs in the general order in which they were formed.

FIG. 5 illustrates in block diagram form a logical process, generally designated 30, underlying the implementation of each of the aforementioned methods for carrying out the present invention. The logical process 30 can be divided into two separate subprocesses. A first subprocess, generally designated 41, basically (1) collects and formats raw input and output data pertaining to such operation of such mechanism and stores the formatted data onto the circular buffer and (2) determines when any one or more of such distinct events occur. A second subprocess, generally designated 72, basically transfers the formatted data from the circular buffer to the memory device. The logical process as set forth hereinafter pertains to the method for carrying out the first embodiment (i.e., when data relating to only one of such distinct events is to be recorded). When data relating to more than one of such distinct events is to be recorded as set forth in the method for carrying out the presently preferred second embodiment, the logical process 30 is duplicated for each such distinct event.

Commencing with the first subprocess 41, raw input and/or output data pertaining to such operation of such mechanism is the input to block 42. Such raw data is formatted and then stored temporarily on the circular buffer. The circular buffer continuously stores a preset duration's worth of both the formatted data elements and the index numbers corresponding to the formatted data elements; the preset duration directly corresponding to the preset number previously mentioned. For example, assuming the preset duration is ten seconds, the circular buffer always stores a last ten second period's worth of formatted data elements. The oldest formatted data element is continuously replaced with the most recent formatted data element. The output of the block 42 is the newest index number (i.e., most recent index number) stored on the circular buffer.

The retain event log flag and the event active flag are the inputs to block 43. If the formatted data elements for such distinct event is to be retained within the memory device when such distinct event occurs, the retain event log flag is set to true. The event active flag is set to true when such distinct event occurs. Otherwise, the event active flag is set to false. When both the retain event log and the event active flags are set to true, the timer of predetermined duration activates for the predetermined duration. The output of the block 43 is a state of the timer, the timer being either activated or deactivated.

The newest index number and the state of the timer are the inputs to block 44. The outputs of the block 44 are a save log flag and a log index number. When the timer deactivates (i.e., when the predetermined time period ends), the save log flag is set to true and the log index number is set to the newest index number (i.e., the log index number points to a last data element on the circular buffer to be transferred to the memory device). The save log flag when set to true indicates that the formatted data elements relating to such distinct event shall be transferred to the memory device.

Referring now to the second subprocess 72, the save log flag and the log index number are the inputs to block 73. The outputs of the block 73 are a current index number and the stop index number. When the save log flag is set to true, the stop index number is set equal to the log index number. The start index number is calculated as the difference between the stop index number plus one less the log length. The current index number is initially the start index number.

The stop index number from the block 73 and the current index number from block 75 are the inputs to block 74. The output of the block 74 is a transfer complete flag. The transfer complete flag indicates whether all of the formatted data elements stored on the circular buffer between and including the start and stop index numbers have been transferred to the memory device. When set to true, the transfer is complete. Otherwise, the transfer complete flag is set to false.

The transfer complete flag, the current index from the block 73, and the formatted data elements stored on the circular buffer are the inputs to the block 75. The outputs of the block 75 are the save log flag, the incremented current index number, and the formatted data elements to be transferred to and recorded within the memory device. With the current index number initially set to the start index number as indicated by the block 73, the transfer complete flag is set to false. The data element to which the current index number is assigned is then transferred from the circular buffer to the memory device as shown in the block 75. The current index number is then incremented to the next index number (e.g., to the start index number plus one) and fed back to the block 74. If the stop index number is greater than or equal to the current index number as incremented, the block 74 shows that the transfer complete flag remains false. The data element to which the current index number as incremented is assigned is then transferred to the memory device as shown in the block 75. The transfer of formatted data elements continues in this manner until the current index number as incremented is greater than stop index number at which point the transfer complete flag is set to true, as shown in the block 74. The save log flag is then set to false indicating that all of the formatted data elements relating to such distinct event have been recorded within the memory device and that the process 30 is ready for the next occurrence of such distinct event.

It should be noted that care must be taken in ascertaining where on the circular buffer the formatted data elements start and stop for such distinct event and whether the formatted data elements have been stored contiguously or whether they wrap around from an end to a beginning of the circular buffer. Those persons skilled in the art of programming with circular buffers should easily be able to determine and manipulate the start, stop and current index numbers so as to ensure that the formatted data elements transfer in the proper sequence.

It should further be noted that although the present event history data recorder was developed to be used with passenger transit vehicles, the instant invention may be easily applied to other mechanisms including aircraft, water craft, automobiles, buses, railcar train consists, biomedical instruments, and a multitude of other machines.

While the presently preferred embodiment and various additional alternative embodiments for carrying out the instant invention have been set forth in detail in accordance with the Patent Act, those persons skilled in the data recorder art to which this invention pertains will recognize various alternative ways of practicing the invention without departing from the spirit and scope of the appended claims.

Accordingly, to promote the progress of science and useful arts, we secure for ourselves by Letters Patent for a limited time exclusive rights to all subject matter embraced by the following claims.

We claim:

1. An event history data recorder for recording data relating to a distinct event and pertaining to operation of a mechanism preceding and following each occurrence of such distinct event, said recorder comprising:

(a) a means for collecting data pertaining to such operation of such mechanism and relating to such distinct event and for formatting such collected data into a sequence of data elements, said data collecting and formatting means further includes means for assigning sequentially and incrementally an index number to each of said data elements as such collected data is formatted into said sequence of data elements so as to form a sequence of index number-data element units;

(b) a circular buffer linked to said collecting and formatting means for temporarily storing a preset number of said data elements, said data elements being continuously stored on said circular buffer as a newest data element continuously writes over an oldest data element as a storage limit of said circular buffer is reached and as said circular buffer so continuously stores, said circular buffer includes means for temporarily storing said preset number of said index numbers so that said index number-data element units are continuously stored on said circular buffer as a newest index number-data element unit as said storage limit of said circular buffer is reached and as said circular buffer so continuously stores;

(c) a timer of predetermined duration activated upon each occurrence of such distinct event for said predetermined duration;

(d) a memory device for retaining said data elements and from which said data elements can be accessed for analysis of such operation of such mechanism surrounding such distinct event; and (e) a means, connected to said timer, for transferring said data elements from said circular buffer to said memory device, said transferring means includes means for denoting a stop index number, said index number contained within said index number-data element unit being stored onto said circular buffer at an instant said timer deactivates and a means for denoting a start index number plus one less a preselected number;

wherein for each occurrence of such distinct event, said preselected number of said data elements stored prior to, and including, said instant said timer deactivates is transferred by said transferring means from said circular buffer to said memory device thereby forming a data log within said memory device from which said data elements recorded therein may be accessed for analysis of such operation of such mechanism.

2. The event history data recorder as recited in claim 1 wherein said data collecting and formatting means includes a computer, a plurality of sensors and an analog to digital converter, said plurality of sensors for monitoring and generating analog signals corresponding to such operation of such mechanism relating to such distinct event, said analog to digital converter for converting said analog signals into corresponding digital binary code, and said computer for formatting said digital code into said data elements.

3. The event history data recorder as recited in claim 2 wherein said transferring means includes a computer.

4. The event history data recorder as recited in claim 3 wherein said memory device is a random access memory chip.

5. The event history data recorder as recited in claim 4 wherein said data log is updated each occurrence of such distinct event.

6. The event history data recorder as recited in claim 4 wherein said memory device is an electrically erasable programmable read only memory chip.

7. The event history data recorder as recited in claim 4 wherein said data log formed when such distinct event initially occurred is retained and a new data log is formed within said memory device for each subsequent occurrence of such distinct event until a storage capacity of said memory device is reached at which time said data logs are updated in an order in which said data logs were formed.

8. A method for the selective recordation of data relating to a distinct event and pertaining to operation of a mechanism preceding and following each occurrence of such distinct event, said method comprising the steps of:

(a) collecting data pertaining to such operation of such mechanism and relating to such distinct event;

(b) formatting such collected data into a sequence of data elements;

(c) assigning sequentially and incrementally to each of said data elements an index number thereby forming a sequence of index number-data element units;

(d) storing temporarily on a circular buffer a preset number of said index number-data element units as a newest index number-data element unit continuously writes over an oldest index number-data element unit as a storage limit of said circular buffer is reached and as said circular buffer so continuously stores;

(e) setting a retain event log flag to true when said data elements relating to such distinct event are to be retained in a memory device;

(f) setting an event active flag to true when such distinct event occurs;

(g) activating a timer of predetermined duration when both said retain event log and said event active flags are set to true;

(h) denoting a stop index number as said index number contained within said index number-data element unit being stored onto said circular buffer at an instant said timer deactivates upon expiration of said predetermined duration;

(i) denoting a start index number as said stop index number plus one less a preselected number; and (j) for each occurrence of such distinct event, transferring from said circular buffer to said memory device said data elements located between and including said start and said stop index numbers thereby forming a data log from which said data elements relating to such distinct event may be accessed for analysis of such operation of such mechanism.

9. The method for the selective recordation of data as recited in claim 8 wherein, after said transferring step, said method further includes the step of updating said data log each occurrence of such distinct event.

10. The method for the selective recordation of data as recited in claim 8 wherein, after said transferring step, said method further includes the steps of retaining said data log formed when such distinct event initially occurred; forming a new data log within said memory device for each subsequent occurrence of such distinct event; and when insufficient space within said memory device exists, updating said data logs in an order in which said data logs were formed.

11. An event history data recorder for recording data relating to a plurality of distinct events and pertaining to operation of a mechanism preceding and following each occurrence of each such distinct event, said recorder comprising:

(a) a means for collecting data pertaining to such operation of such mechanism and relating to each such distinct event and for formatting such collected data into a sequence of data elements for each such distinct event for which data is to be recorded, one said data element from one such distinct event being formed nearly coincidently as another one said data element from each of all other such distinct events such that said nearly coincidently formed data elements constitute a set of temporally related data elements;

(b) a circular buffer, linked to said collecting and formatting means, having a plurality of tracks each of which is designated for storing temporarily a preset number of said data elements relating to one of such distinct events so that said data elements relating to such distinct events are aligned to form said sets of temporally related data elements, said sets of temporally related data elements being continuously stored on said circular buffer as a newest set of temporally related data elements continuously writes over an oldest set of temporally related data elements as a storage limit of said circular buffer is reached and as said circular buffer so continuously stores;

(c) a timer of predetermined duration for each such distinct event so that as each such distinct event occurs said timer individually corresponding thereto activates for said predetermined duration;

(d) a memory device having a plurality of memory locations each of which is dedicated to retaining said data elements temporarily stored on one of said tracks of said circular buffer when such distinct event to which said data elements relate occurs; and (e) a means, connected to each of said timers, for transferring said data elements from said tracks of said circular buffer to said dedicated memory locations;

wherein as said timers individually corresponding to such distinct events deactivate, said transferring means transfers from said tracks to said dedicated memory locations a preselected number of said data elements for each of such distinct events so occurred thereby essentially forming within each of said dedicated memory locations a data log from which said data elements relating to one of such distinct events may be accessed for analysis of such operation of such mechanism.

12. The event history data recorder as recited in claim 11 wherein:

(a) said data collecting and formatting means further includes means for assigning sequentially and incrementally an index number to each of said sets of temporally related data elements as such collected data is formatted into said sequences of data elements for such distinct events so as to form a sequence of index number-set units;

(b) said circular buffer includes means for temporarily storing said preset number of said index numbers on another track of said circular buffer so that said index number-set units are continuously stored on said circular buffer as a newest index number-set unit continuously writes over an oldest index number-set unit as said storage limit of said circular buffer is reached and as said circular buffer so continuously stores; and (c) said transferring means further includes means for,
(i) denoting a stop index number for each such distinct event so occurred as said index number contained within said index number-set unit being stored onto said circular buffer when said timer individually corresponding to such distinct event deactivates, and
(ii) denoting a start index number for each such distinct event so occurred as said stop index number plus one less said preselected number, said stop and start index numbers being generated in pairs where each pair corresponds to one of such distinct events;

wherein said transferring means for each such distinct event so occurred transfers said data elements located between and including said start and stop index numbers from said tracks to said dedicated memory locations.

13. The event history data recorder as recited in claim 12 wherein said data collecting and formatting means includes a computer, a plurality of sensors and an analog to digital converter, said plurality of sensors for monitoring and generating analog signals corresponding to such operation of such mechanism relating to each such distinct event, said analog to digital converter for converting said analog signals into corresponding digital binary code, and said computer for formatting said digital code into said data elements.

14. The event history data recorder as recited in claim 13 wherein said transferring means includes a computer.

15. The event history data recorder as recited in claim 14 wherein said memory device is a random access memory chip.

16. The event history data recorder as recited in claim 15 wherein said data log is updated each occurrence of such distinct event to which said data log is dedicated.

17. The event history data recorder as recited in claim 16 wherein any one or more of such distinct events may be either selected or deselected for recordation.

18. The event history data recorder as recited in claim 15 wherein said memory device is an electrically erasable programmable read only memory chip.

19. The event history data recorder as recited in claim 15 wherein said data log formed when such distinct event to which said data log is dedicated initially occurred is retained and a new data log is formed within each of said memory locations for each subsequent occurrence of such distinct event to which said new data log is dedicated until a storage capacity of said memory locations is reached at which time said data logs for each of such distinct events are updated in a general order in which said data logs were formed.

20. A method for the selective recordation of data relating to a plurality of distinct events and pertaining to operation of a mechanism preceding and following each occurrence of each such distinct event, said method comprising the steps of:

(a) collecting data pertaining to such operation of such mechanism and relating to each such distinct event;

(b) formatting such collected data into a sequence of data elements for each such distinct event for which data is to be recorded, one said data element from one such distinct event being formed nearly coincidently as another one said data element from each of all other such distinct events such that said nearly coincidently formed data elements constitute a set of temporally related data elements;

(c) assigning sequentially and incrementally an index number to each of said sets of temporally related data elements so as to form a sequence of index number-set units;

(d) storing temporarily on one of a plurality of tracks of a circular buffer said assigned index numbers and on each of all other said tracks a preset number of said data elements relating to one of such distinct events so that said assigned index numbers and said data elements relating to such distinct events are aligned to form said sequence of index number-set units, said index number-set units being continuously stored on said circular buffer as a newest index number-set unit continuously writes over an oldest index number-set unit as a storage limit of said circular buffer is reached and as said circular buffer so continuously stores;

(e) for each of such distinct events, setting a retain event log flag to true when said data elements relating to such distinct event are to be retained in a memory location dedicated to such distinct event, said memory location being one of a plurality of memory locations within a memory device each of said memory locations being dedicated to one of such distinct events;

(f) for each of such distinct events, setting an event active flag to true when such distinct event occurs;

(g) for each of such distinct events, activating a timer of predetermined duration when both said retain event log and said event active flags for such distinct event are set to true;

(h) for each such distinct event so occurred, denoting a stop index number as said index number contained within said index number-set unit being stored onto said circular buffer at an instant said timer corresponding to such distinct event deactivates;

(i) for each such distinct event so occurred, denoting a start index number as said stop index number plus one less a preselected number; and (j) for each such distinct event so occurred, transferring said data elements located between and including said start and stop index numbers from said track to corresponding said dedicated memory location for each occurrence of such distinct event thereby essentially forming within said dedicated memory location a data log from which said data elements relating to such distinct event may be accessed for analysis of such operation of such mechanism.

21. The method for the selective recordation of data as recited in claim 20 wherein, after said transferring step, said method further includes the step of updating said data log each occurrence of such distinct event.

22. The method for the selective recordation of data as recited in claim 20 wherein, after said transferring step, said method further includes the step of retaining said data log formed when such distinct event to which said data log is dedicated initially occurred; forming a new data log within said memory location for each subsequent occurrence of such distinct event to which said new data log is dedicated; and, when insufficient space within said dedicated memory location exists, updating said data logs in a general order in which said data logs were formed.

* * * * *